(12) United States Patent
Brooks

(10) Patent No.: US 8,524,058 B2
(45) Date of Patent: Sep. 3, 2013

(54) LOW POWER AMPEROMETRIC PROBE

(75) Inventor: Michael Brooks, Yalding (GB)

(73) Assignee: Siemens Industry, Inc., Alpharetta, GA (US)

( * ) Notice: Subject to any disclaimer, the term of this patent is extended or adjusted under 35 U.S.C. 154(b) by 160 days.

(21) Appl. No.: 12/864,107

(22) PCT Filed: Jan. 20, 2009

(86) PCT No.: PCT/EP2009/050594
§ 371 (c)(1),
(2), (4) Date: Feb. 9, 2011

(87) PCT Pub. No.: WO2009/092708
PCT Pub. Date: Jul. 30, 2009

(65) Prior Publication Data
US 2011/0127163 A1    Jun. 2, 2011

Related U.S. Application Data

(60) Provisional application No. 61/022,942, filed on Jan. 23, 2008.

(51) Int. Cl.
*G01N 27/26*    (2006.01)

(52) U.S. Cl.
USPC ............................ 204/408; 204/400; 324/431

(58) Field of Classification Search
USPC ................................. 204/408, 400; 324/431
See application file for complete search history.

(56) References Cited

U.S. PATENT DOCUMENTS

| | | | |
|---|---|---|---|
| 4,227,984 A | 10/1980 | Dempsey et al. | |
| 6,238,555 B1 * | 5/2001 | Silveri et al. | 210/143 |
| 7,189,314 B1 | 3/2007 | Pace et al. | |
| 2002/0042686 A1 * | 4/2002 | Kobayashi et al. | 702/100 |

FOREIGN PATENT DOCUMENTS

| | | |
|---|---|---|
| EP | 0543770 B1 | 8/1997 |
| WO | 01/57513 A2 * | 8/2001 |
| WO | 0157513 A3 | 2/2002 |
| WO | WO 03/087802 A2 * | 10/2003 |
| WO | 03087802 A3 | 10/2004 |
| WO | WO 2007/026152 A1 * | 3/2007 |

OTHER PUBLICATIONS

Bard and Faulkner, Electrochemical Methods, 1980 John Wiley & Sons, Inc.*

* cited by examiner

*Primary Examiner* — Luan Van
*Assistant Examiner* — Steven Rosenwald

(57) ABSTRACT

An amperometric probe suitable for monitoring chlorine levels in water is described. The probe has low power consumption and maintenance requirements rendering it particularly suitable for long periods of operation in remote locations with portable power supplies.

18 Claims, 3 Drawing Sheets

LOW POWER AMPEROMETRIC PROBE

CROSS REFERENCE TO RELATED APPLICATIONS

This application is a U.S. national stage application and claims the benefit under 35 U.S.C. §371 of International Application No. PCT/EP2009/050594 filed on Jan. 20, 2009, entitled LOW POWER AMPEROMETRIC PROBE, which claims the benefit under 35 U.S.C. §119(e) of U.S. Provisional Application Ser. No. 61/022,942 entitled LOW POWER POTENTIONSTAT CIRCUIT, filed on Jan. 23, 2008 each of which is herein incorporated by reference in their entirety and to which this application claims the benefit of priority.

The practice of adding chlorine to water to act as disinfectant has been well established for many years. There is an associated need to analyse water for chlorine content which has traditionally been met using techniques that involve chemical reagents and buffering. These techniques are time consuming and expensive and do not readily lend themselves to rapid, in-field testing by mobile personnel.

There exists a long standing desire for a method of chlorine analysis that does not involve chemical reagents and can be conveniently carried out in the field, for example, by agents of the water supply industries.

The current trend in the water supply industries is an increasing demand for remote systems that are able to monitor levels of species such as chlorine remotely, with little and infrequent human intervention. Ideally a system is able to perform measurements automatically at pre-determined locations and transmit data so obtained to a central processing site.

The determination of analyte concentration in a solution by amperometry is well known. In such analyses, the electric current generated in a suitable chemical reaction involving the analyte is measured and used as an indication of analyte concentration.

The determination of chlorine concentration in a solution by amperometry is possible but a system which meets the water industries' requirements, of remote, automated operation with long periods between maintenance needs to be robust and reliable over such periods. Such systems are typically powered by stand alone power cells or batteries and it is essential that the systems place low demands on these power supplies.

An object of the invention is to provide a system meeting these requirements.

According to the invention, apparatus for determining the level of chlorine in water comprises the features set out in claim 1 attached hereto.

The invention will now be described by non-limiting example, with reference to the following figures in which.

Figure 1:
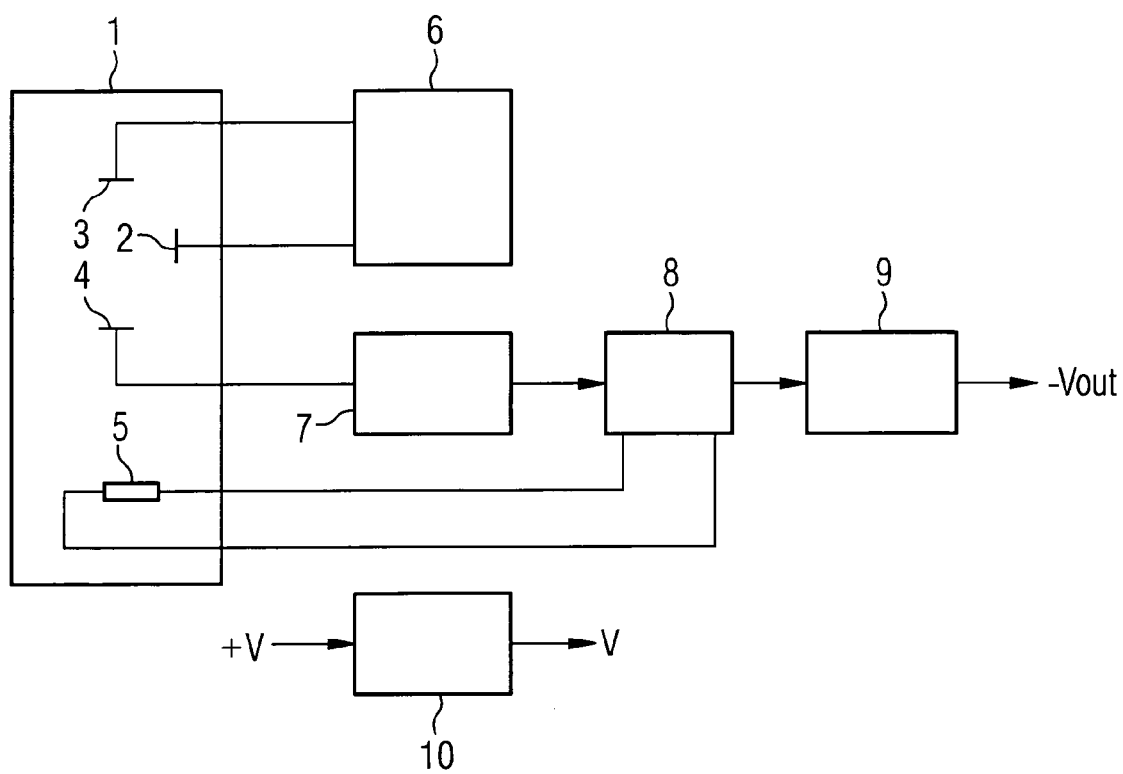
FIG. 1 shows a schematic block diagram of apparatus according to the invention.

Referring to FIG. 1, apparatus according to the invention comprises an amperometric probe 1, having a reference electrode 2, a counter electrode 3 and a working electrode 4. The probe 1 also includes a thermistor 5.

The apparatus further includes a bias voltage module 6 which drives the counter electrode 3 and maintains the bias voltage at the reference electrode 2.

The probe is rendered selective to species of interest by an species-selective barrier (e.g. an ion selective membrane, not shown) between the working electrode and the sample solution.

The current flowing in the working electrode 4 is converted to a voltage by a current to voltage conversion module 7. Said voltage is then adjusted for temperature of the sample by temperature correction module 8 with reference to thermistor 5.

Finally, a gain adjustment module 9 scales the temperature corrected voltage to a range suitable for further processing, for example to the appropriate range of an analogue to digital converter being used to convert the measurement to a digital form.

Some of the electronic components of the apparatus require a positive and negative voltage. However, a preferred embodiment of the invention is powered by a simple (positive) D.C. power supply (not shown). In such an embodiment, a voltage inverter module 10 provides a negative voltage equal in magnitude to the supplied positive voltage.

Figure 2:
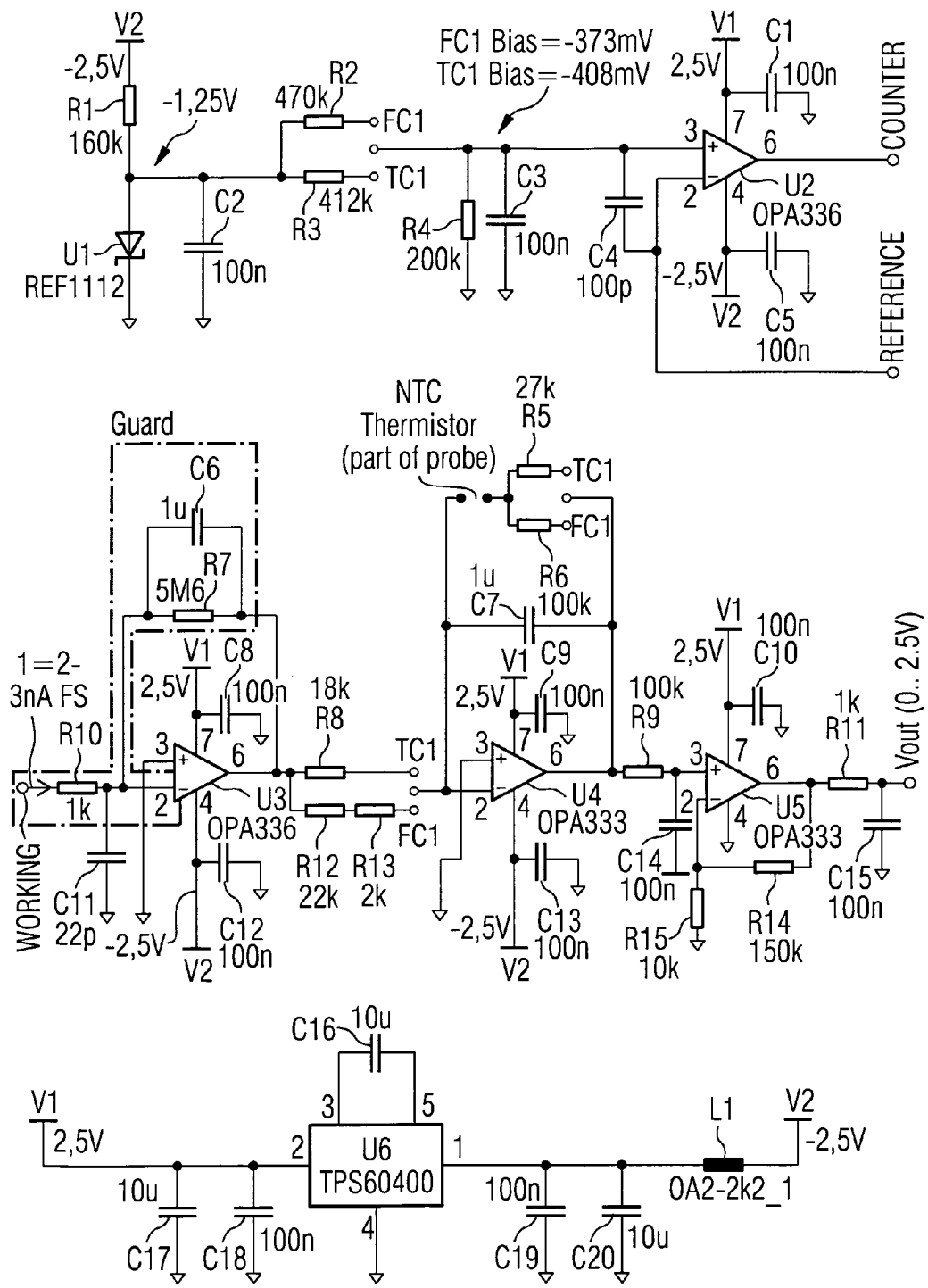
FIG. 2 shows a detailed circuit diagram of the electrical components of the invention.

Referring to FIG. 2, a −2.5V power supply is generated from a +2.5V system supply using a charge pump inverter U6 (TPS60400). This device requires three external capacitors to operate (C17, C16 & C20) and has been chosen for its low quiescent current requirement. Capacitors C18 and C19 provide additional decoupling. L1 is a ferrite bead, and is intended to give additional filtering of the output ripple voltage.

A micro-power shunt voltage reference, U1, produces a voltage of −1.25V. This device has a capacitor, C2, across the output to maintain stability. The reference voltage is then divided by a potential divider to provide the bias voltage for the probe. The divider for the probe bias voltage is switchable as the circuit will operate with two types of probe as follows:

| | |
|---|---|
| Free Chlorine Probe (FC1) | Bias −373 mV |
| Total Chlorine Probe (TC1) | Bias −408 mV |

The selected bias voltage is applied to the non-inverting input of amplifier U2. The output of this amplifier drives the Counter electrode, and the inverting input is connected to the Reference electrode. This amplifier will drive the Counter electrode voltage to a level required to maintain the Reference electrode at the selected bias potential. The amplifier used (OPA336) has very low quiescent current, and low offset voltage (±125 μV max).

The measurement current flows into the Working electrode and is filtered by R10 and C11. An op-amp configured as a transimpedance amplifier (U3) then converts this current to a voltage, the transfer characteristic is as follows:

$$V = -I\text{in} \times R7$$

For an input current of 3 nA (highest full scale probe current) the output of this stage will be 19 mV.

The amplifier used for U3 is an OPA336, specifically chosen for low input bias current (Ib), low voltage offset (Vos) and low quiescent current. Capacitors C8 and C12 provide local decoupling for the amplifier, and C6 maintains amplifier stability.

Figure 3:
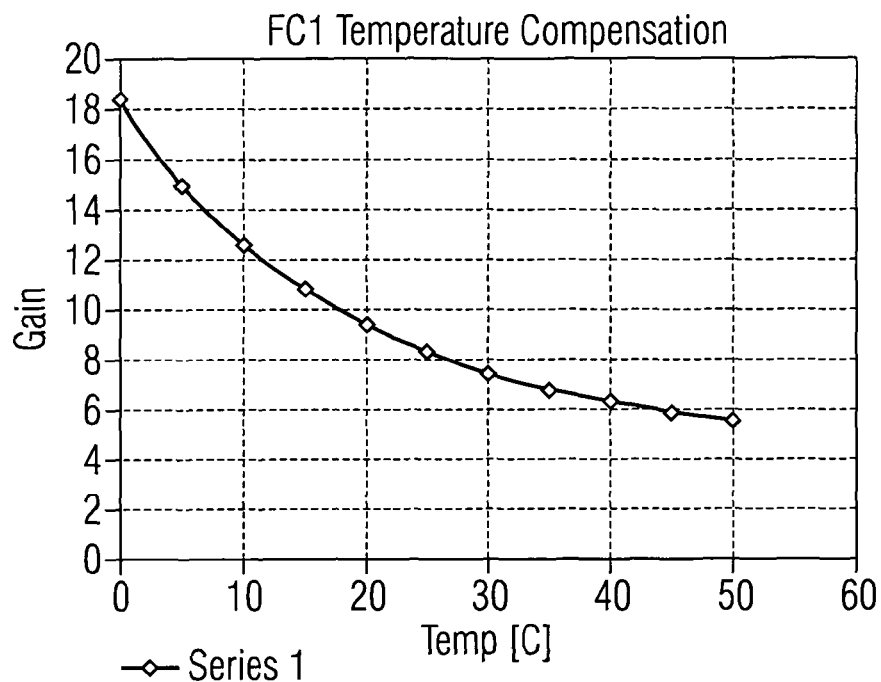
FIGS. 3 and 4 show transfer characteristics for a temperature compensation module forming part of the invention.
Figure 4:
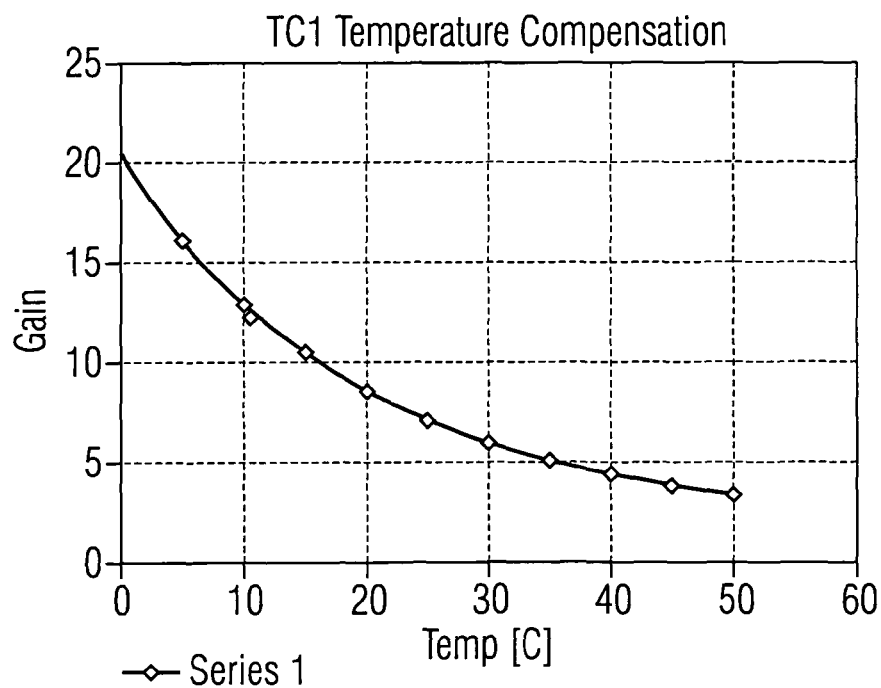

The temperature compensation is performed by an inverting amplifier (U4) with a thermistor in its feedback loop. The thermistor is physically part of the probe and its resistance ($R_T$) will change with the water temperature. The compensation is different for the TC1 and FC1 probes so links are provided to change resistor values. The two possible transfer characteristics for this stage are given by the following equations, and are also shown graphically in FIG. 3 and FIG. 4:

TC1:
$$Vout = -Vin((R5+RT)/R8)$$

FC1:
$$Vout = -Vin((R6+RT)/(R12+R13))$$

This is an inverting stage and the input is a negative measurement voltage; the output from this stage is therefore a positive voltage. A single pole filter consisting of R9 and C14 is applied to the output. Capacitors C9 and C13 provide local decoupling, and C7 ensures amplifier stability. The amplifier used in this stage (OPA333) has low voltage offset (Vos) and low quiescent current.

The final stage (U5) is a non-inverting amplifier that is used to scale the voltage to the ADC input range. This stage has a fixed gain of 16 (1+R14/R15), and uses an OPA333 amplifier (U5) with low voltage offset and quiescent current. The amplifier has a single +2.5V power supply so the output cannot be driven below ground which may damage the ADC.

The component values used in the output filter (R11 and C15) are designed to meet the requirements of the ADC input stage.

This circuit is designed for the lowest possible power consumption while still meeting the very demanding measurement requirements. An estimate of the typical operating current is shown in Table 4.1. At 2.5V the total current of 171 μA gives a power consumption of 428 μW. This low power consumption means that the circuit could run continuously for long periods in a battery operated instrument.

TABLE 1

Estimated Operating Current

| Circuit section | I (μA) |
|---|---|
| Charge pump inverter (U6) | 65 μA |
| Voltage reference (U1) | 16 μA |
| Counter electrode drive amplifier (U2) | 20 μA |
| Transimpedance amplifier (U3) | 20 μA |
| Temperature compensation amplifier (U4) | 17 μA |
| Fixed gain amplifier (U5) | 33 μA |
| Total | 171 μA |

The invention claimed is:

1. An apparatus for determining the concentration of a species in a sample, the apparatus comprising:
    a probe having a reference electrode, a counter electrode, a working electrode and a thermistor;
    a bias voltage module including a voltage reference and a counter electrode drive amplifier, the bias voltage module arranged to provide a constant voltage between the reference electrode and the working electrode;
    a transimpedence amplifier arranged to produce a measured voltage as a measure of current flowing between the counter electrode and the working electrode;
    a temperature compensation amplifier arranged to adjust the measured voltage to produce a temperature corrected voltage in response to changes in the resistance of the thermistor;
    a fixed gain amplifier arranged to re-scale the temperature corrected voltage;
    the probe having a power consumption of about 428 μW when operated at 2.5V.

2. The apparatus of claim 1, further comprising a charge pump inverter arranged to produce a negative voltage equal in magnitude to a supplied positive voltage.

3. The apparatus of claim 1, further comprising a species selective barrier arranged between the working electrode and a sample solution.

4. The apparatus of claim 3, wherein the reference voltage is divided by a potential divider that is switchable between a first sensing mode providing a first bias and a second sensing mode providing a second bias voltage.

5. The apparatus of claim 4, wherein when operated in the first sensing mode, the apparatus measures a concentration of free chlorine in the sample.

6. The apparatus of claim 5, wherein when operated in the second sensing mode, the apparatus measures a concentration of total chlorine in the sample.

7. The apparatus of claim 6, wherein the first bias voltage is about 480 mV.

8. The apparatus of claim 7, wherein the second bias voltage is about 373 mV.

9. The apparatus of claim 8, wherein the temperature compensation amplifier is switchable between a first mode of compensation and a second mode of compensation.

10. The apparatus of claim 9, wherein the first mode of compensation is configured to compensate for changes in a solution temperature when the apparatus is operating in the first sensing mode.

11. The apparatus of claim 10, wherein the second mode of compensation is configured to compensate for changes in a solution temperature when the apparatus is operating in the second sensing mode.

12. The apparatus of claim 11, wherein the apparatus is powered by a battery.

13. The apparatus of claim 12, further comprising an analog to digital converter.

14. The apparatus of claim 1, wherein the bias voltage module has a current consumption of about 36 μA.

15. The apparatus of claim 1, wherein the transimpedence amplifier has a current consumption of about 20 μA.

16. The apparatus of claim 1, wherein the temperature compensation amplifier has a current consumption of about 17 μA.

17. The apparatus of claim 1, wherein the fixed gain amplifier has a current consumption of about 17 μA.

18. The apparatus of claim 2, wherein the charge pump inverter has a current consumption of about 65 μA.

* * * * *